United States Patent [19]
Volsey, II

[11] Patent Number: 5,865,186
[45] Date of Patent: Feb. 2, 1999

[54] SIMULATED HEATED CIGARETTE

[76] Inventor: Jack J Volsey, II, 589 Douglas Dr., Rock Springs, Wyo. 82901

[21] Appl. No.: 859,889

[22] Filed: May 21, 1997

[51] Int. Cl.$^6$ ........................................................ A24F 1/00
[52] U.S. Cl. ............................ 131/194; 196/273; 196/359
[58] Field of Search ..................................... 131/194, 196, 131/215.2, 359, 361, 273, 360, 363, 364

[56] References Cited

U.S. PATENT DOCUMENTS

| | | | |
|---|---|---|---|
| 4,892,109 | 1/1990 | Strubel | 131/194 |
| 5,540,241 | 7/1996 | Kim | 131/215.2 |

*Primary Examiner*—John G. Weiss
*Assistant Examiner*—Charles W. Anderson
*Attorney, Agent, or Firm*—Risto A. Rinne, Jr.

[57] ABSTRACT

A simulated cigarette is provided that includes an elongated deformable cylindrical body that is open at both ends thereof. At least two capsules, at least one of which being rupturable, are included in the cylindrical body. Each capsule contains a potentially chemically reactive substance which, when admixed together, react chemically to produce an exothermic chemical reaction, the heat of which is used to elevate the temperature of a vapor within the simulated cigarette. The heated vapor is inhaled by a user and in the process passes through a substance from which it absorbs either a flavoring, medicine, or a quantity of nicotine. A one-way valve is provided which permits the vapor to travel in only one direction through the simulated cigarette.

20 Claims, 1 Drawing Sheet

SIMULATED HEATED CIGARETTE

BACKGROUND OF THE INVENTION

1. Field of the Invention:

The present invention, in general, relates to apparatus used to simulate the sensation of smoking a cigarette and, more particularly, to a chemically heated simulated cigarette.

Simulated types of cigarettes are known. In general they fail to satisfy the need to provide a cigarette that does not produce smoke (which is an objectionable by-product that is now prohibited in most public places because of the noxious and toxic emissions) while still providing the sensation of being able to inhale a flavored vapor that contains a controlled predetermined amount of any desired substance including nicotine and that also is heated. In addition the ideal simulated cigarette would be safe and easy to use and would not introduce pollutants into the environment.

Accordingly there exists today a need for a simulated heated cigarette that allows for the flavoring of the vapor to be inhaled, control of the substances to be inhaled, heats the vapor to be inhaled, and does not produce visible smoke as a by-product that is also safe to use and is environmentally non-polluting.

2. Description of Prior Art:

Simulated cigarettes are, in general, known. For example, the following patents describe various types of these devices:

U.S. Pat. No. 2,907,686 to Siegel, Oct. 6, 1959;
U.S. Pat. No. 3,587,573 to Flack, Jun. 28, 1971;
U.S. Pat. No. 4,149,548 to Bradshaw, Apr. 17, 1979;
U.S. Pat. No. 4,687,008 to Houck, Aug. 18, 1987;
U.S. Pat. No. 4,892,109 to Strubel, Jan. 9, 1990;
U.S. Pat. No. 5,135,009 to Muller et al., Aug. 4, 1992;
U.S. Pat. No. 5,141,004 to Porenski, Aug. 25, 1992;
U.S. Pat. No. 5,443,560 to Deevi et al., Aug. 22, 1995;
U.S. Pat. No. 5,472,001 to Nicholson, Dec. 5, 1995; and
U.S. Pat. No. 5,540,241 to Kim, Jul. 30, 1996.

While the structural arrangements of the above described devices, at first appearance, have similarities with the present invention, they differ in material respects. These differences, which will be described in more detail hereinafter, are essential for the effective use of the invention and which admit of the advantages that are not available with the prior devices.

OBJECTS AND SUMMARY OF THE INVENTION

It is an important object of the present invention to provide a simulated heated cigarette that heats the vapor to be inhaled.

It is also an object of the invention to provide a simulated heated cigarette that does not produce smoke.

Another object of the invention is to provide a simulated heated cigarette that does not produce noxious or toxic emissions.

Still another object of the invention is to provide a simulated heated cigarette that contains a predetermined amount of a predetermined flavor-enhancing substance.

Yet another object of the invention is to provide a simulated heated cigarette that contains a predetermined amount of a predetermined therapeutic substance.

Yet another very important object of the invention is to provide a simulated heated cigarette that contains a predetermined amount of nicotine.

Briefly, a simulated heated cigarette that is constructed in accordance with the principles of the present invention has an elongated deformable body that is sufficiently open at both ends to allow the passage of a vapor through the cigarette to be inhaled by a user. At least two capsules, at least one of which being crushable, each contain a chemical substance, which when combined produce an exothermic chemical reaction to heat the vapor to be inhaled. Flavorings, medicines, tobacco, nicotine, screens, and filters are used to affect and to modify the vapor as desired.

DETAILED DESCRIPTION OF THE INVENTION

Figure 1:
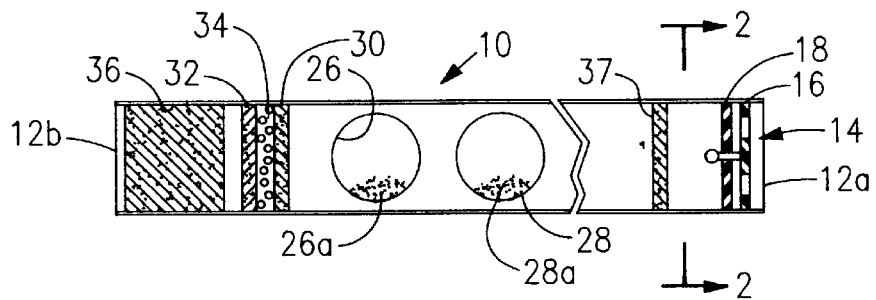
FIG. 1 is a side view in cross-section of the simulated heated cigarette showing two adjacent crushable capsules side by side.

Referring on occasion to all of the FIGURE drawings is shown, a simulated heated cigarette, identified in general by the reference numeral 10.

A deformable cylinder 12 forms a conduit (tube) for the vapors to be inhaled through. The cylinder 12 has an intake end 12a where ambient air is drawn in by a user (not shown) who draws the vapor into his mouth from an outlet end 12b that is disposed opposite with regard to the intake end 12a. While any suitable material may be used for construction of the cylinder 12, a soft deformable plastic is anticipated to form the tube.

The term vapor as used in this specification refers to the ambient air that has been drawn into the simulated heated cigarette 10 and which has been affected by the simulated heated cigarette in some way. The ambient air that is drawn into the simulated heated cigarette 10 is heated (when the cigarette has been activated) and it may also contain any of a variety of other substances or flavorings as are described in greater detail hereinbelow. Accordingly ambient air refers to the air that exists normally in the environment whereas vapor refers to the ambient air that is drawn into the simulated heated cigarette 10 and which has been affected in some manner by the simulated heated cigarette 10.

Figure 2:
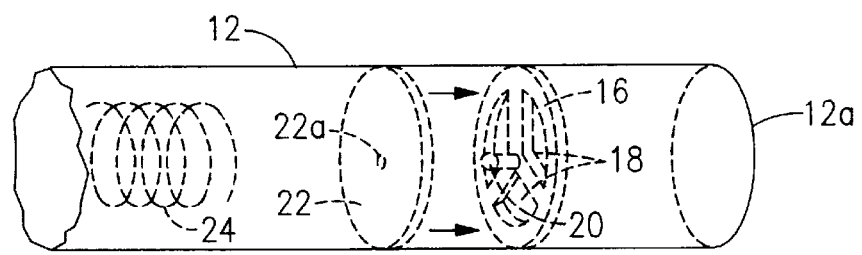
FIG. 2 is an enlarged perspective view of a valve embodied in the simulated heated cigarette shown in FIG. 1 along the lines 2—2 therein and also including a spring absent the FIG. 1 drawing.

The ambient air enters into the intake end 12a of the cylinder 12 by passing through a one-way valve 14 assembly, details of which are shown in greater detail in FIG. 2 and to which view attention is momentarily directed. The valve 14 includes a disk 16, having either one or a plurality of holes 18 therein to allow for passage of the ambient air. The disc 16 can be formed of any desired material although plastic is preferred.

A post 20 having an enlarged end forms a protrusion that can secure a rubber disk 22 thereto, the rubber disk 22 having a hole 22a in the center thereof that is capable of expanding a sufficient amount to allow the hole 22a to pass over the post 20 beyond the protrusion, thus securing it in position.

Other means to better secure the rubber disk 22 about the post 20 to the disk 16 include the possible use of a spring 24. The spring is contained within the cylinder 12 so as to apply a force to the rubber disk 22 thus maintaining it in a position of cooperation adjacent to the disk 16.

During use the rubber disk 22 is disposed adjacent to the disk 16. The rubber disk 22 is flexible and when the user inhales he creates a partial vacuum within the cylinder 12. Ambient air, which is now under greater pressure than the partial vacuum within the cylinder 12, enters into the intake end 12a of the cylinder 12 and forces the rubber disk 22 of the valve 14 assembly to retreat from the disk 16, thus allowing the passage of ambient air through the holes 18 and further into the body of the cylinder 12.

The valve 14 restricts air flow to one direction only, namely entering from the intake end 12a and exiting from the outlet end 12b. To generally prevent the escape of any heated air (as is described in greater detail hereinbelow) out through the intake end 12a, the rubber disk 22 normally bears against the disk 16 covering the holes 18. This prevents the escape of any substantial amount of vapors (air) out through the intake end 12a. Any cause leading to an increase of pressure within the cylinder 12, such as would arise if the user were to attempt to blow into the outlet end 12b of the cylinder 12 or if a temperature rise (as is described in greater detail hereinbelow) were to cause the air within the cylinder 12 to expand, the rubber disk 22 would bear with even greater force upon the disk 16 thus forming an even more effective seal.

The valve 14 assembly is disposed near to the intake end 12a of the cylinder and is preferably recessed in from the intake end 12a a predetermined amount. The predetermined amount depends upon where additional inner support is desired for the cylinder 12 as the valve 14 keeps the cylinder 12 expanded and into a round configuration. This is accomplished because the valve 14 assembly is not compressible when the cylinder 12 is squeezed from the outside. Accordingly the valve 14 assembly keeps the intake end 12a of the cylinder 12 round which aids in maintaining the appearance of the simulated heated cigarette 10.

Returning now to FIG. 1 and on occasion to the remaining FIG. drawings, is shown a first crushable chemical insert 26 adjacent to a second crushable chemical insert 28. The first crushable chemical insert 26 and the second crushable chemical insert 28 are in the form of capsules disposed within the cylinder 12 in such a fashion so as not to obstruct the passage of air around them after they have been crushed. A first substance 26a is contained in the first crushable chemical insert 26 and a second substance 28a is contained in the second crushable chemical insert 28. The first substance 26a and the second substance 28a may be a combination of any desired element, compound, or mixture, in either gaseous, liquid, or solid form such that when the first substance 26a and the second substance 28a are combined, a chemical reaction occurs that also produces heat. Such a chemical reaction is referred to as an exothermic reaction from this point on. When the deformable cylinder 12 is squeezed by the user, generally in the middle of the length of the cylinder 12, the first crushable chemical insert 26 and the second crushable chemical insert 28 are ruptured thus releasing the first substance 26a and the second substance 28a, which are free to combine together in an exothermic reaction producing heat. The compounds produced as a result of the reaction are not generally significant. What is desired is a means to provide a chemical reaction that can produce heat and, accordingly, heat the vapor in the cylinder 12.

In this case both the by-products of the chemical reaction as well as trace amounts of the first substance 26a and the second substance 28a intermingle with the vapor and, accordingly, may be inhaled. Of course in this situation no noxious or toxic substances can be produced by the chemical reaction.

Figure 3:
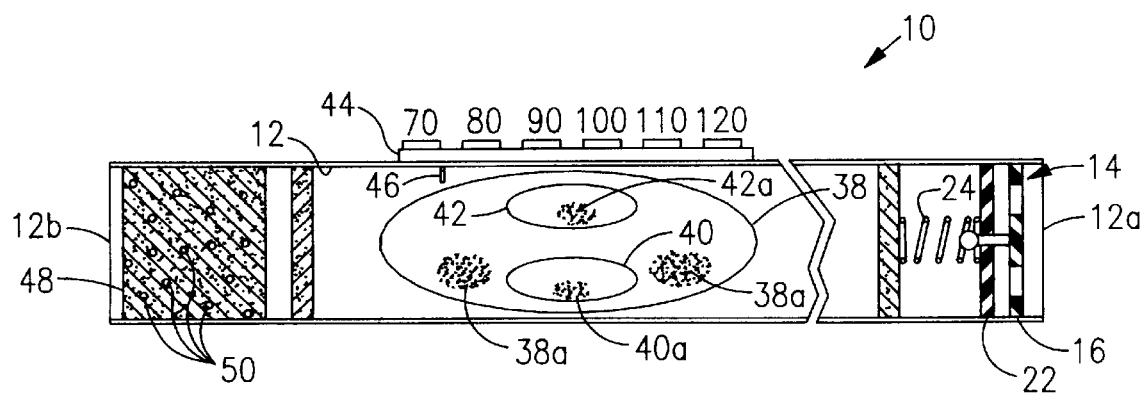
FIG. 3 is a side view in cross-section of the simulated heated cigarette showing a pair of crushable capsules contained within a larger deformable capsule and also showing additional elements of the simulated heated cigarette.

By way of example, one possible combination of substances include a mixture of manganese dioxide and copper oxide (known by the tradename "HOPCALITE") that is disposed as the first substance 26a contained within the first crushable chemical insert 26 and carbon monoxide that is disposed as the second substance 28a contained within the second crushable chemical insert 28. When crushed and mixed the reaction produces heat and carbon dioxide, the latter of which can be safely inhaled. The amount of carbon monoxide is itself limited and is not believed to present a health concern with regard to inhalation. If the possibility of inhalation of the carbon monoxide is deemed to be undesirable, the embodiment as is shown in FIG. 3 and described in greater detail hereinbelow, may safely be used to contain these particular substances.

According to this embodiment the air is inhaled after passing through the chemicals. It is of course necessary to prevent the chemicals themselves from being inhaled. A first screen 30 that is disposed in the cylinder 12 intermediate the first crushable chemical insert 26 and the outlet end 12b of the cylinder 12 is used to prevent the chemicals themselves from being inhaled. The first screen 30 may be constructed much like the screening on a window or a door, or it may be constructed of an interwoven type of a mesh, generally resembling that of steel wool but of a denser composition.

A second screen 32 is shown disposed a predetermined distance from the first screen 30 and may be added if desired. This accomplishes the obvious goal of providing further filtration to the vapor that is being inhaled thus removing additional trace amounts of chemical impurities.

The second screen 32 also provides three unexpected benefits. The first is that, because it impedes the passage of air (vapor), it adds further resistance to the act of inhaling. Accordingly the second screen 32 can be used in concert with the first screen 30 to establish any desired amount of resistance thus more accurately simulating the resistance to inhalation that is encountered when smoking a conventional type of a cigarette (not shown). This allows the simulated heated cigarette 10 to more closely resemble the sensation of smoking the conventional type of a cigarette thus making it a more acceptable, and hence, a more effective device.

The second unexpected benefit encountered is that the second screen 32 when used in concert with the first screen 30 defines a space that is located between the first screen 30 and the second screen 32 that can be used to effectively contain a desired substance 34.

The desired substance 34 is either a flavor enhancer, a therapeutic substance, tobacco, or a nicotine based product, or a combination of the above. The flavor enhancer when used as the desired substance 34 is useful to add flavor to the simulated heated cigarette 10, thus furthering its appeal. For example, spearmint flavoring would liven the taste of the simulated heated cigarette 10.

The therapeutic substance when used as the desired substance 34 is useful to treat patients attempting to withdraw from cigarette smoking as well as to treat patients suffering from a variety of maladies. Any conceivable therapeutic substance that can be inhaled can be dispensed in this manner. For example, medicines used to treat bronchial conditions such as asthma could be so dispensed as well as medicines used to curb the desire for nicotine, or for that matter, to curb the desire for any other drug. Of course, the spacing between the between the first screen 30 and the second screen 32 can be either increased or decreased to accommodate any quantity of the desired substance 34.

Tobacco, when used as the desired substance 34 is useful to satisfy both the pleasure and the cravings of smoking the conventional type of a cigarette but without producing any visible smoke as a by-product. It is the smoke that arises from smoking that contains the many substances believed to be harmful, not only to the user, but to those nearby who may be exposed to "second-hand smoke". Without producing smoke, the heated vapor passes through the tobacco extracting both flavors and nicotine therefrom, thus satisfying both the pleasure associated with the taste sensations of smoking and also the craving for nicotine.

To better extract both the flavors and the nicotine from the tobacco, the vapor must first be heated. The pleasure derived from the inhalation of a "cold" cigarette is indeed limited. Were it not so, then it would be common practice to merely inhale through the tobacco of the conventional type of a cigarette that has not been lighted (ignited). Observation will reveal that this practice is seldom observed. This has proved to be unsatisfactory in terms of extracting an effective level of nicotine, to satisfy the flavor requirements, and also to satisfy the preferred sensation of inhaling a heated vapor similar to that of conventional heated cigarette smoke.

It is believed that such a product, absent smoke, would be acceptable for use in public. With the current trend limiting public places where smoking is permitted, the simulated heated cigarette 10 offers an effective solution to allow the user to indulge himself in public places.

The nicotine based product, when used as the desired substance 34 is useful to satisfy the cravings described above. The nicotine based product may consist of an extract containing nicotine in any desired strength (dosage), such as a nicotine patch. By offering a variety of nicotine dosages a means to taper the user away from his cravings for nicotine by gradually reducing the nicotine strength is provided. As such the simulated heated cigarette 10 provides a method to allow users to quit smoking, and to do so gradually at their own pace and with minimum withdrawal symptoms.

Of course, another method to quit smoking can be achieved by a progressive reduction in the amount of tobacco utilized in the simulated heated cigarette, when tobacco is used as the desired substance 34.

The third unexpected benefit is that the second screen 32 and the first screen 30 tend to keep the cylinder 12 expanded and therefore round. When the cylinder 12 is squeezed the first screen 30 and the second screen exert a force from the inside of the cylinder 12 outward that expands the cylinder 12 back into a more round condition, thus further increasing the appeal of the simulated heated cigarette 10.

A conventional type of a cigarette filter 36 is shown disposed in the cylinder 12 at the outlet end 12b. The filter 36 can be used in place of the first screen 30 and the second screen 32, if desired, or in addition to them.

An inlet screen 37 is disposed between the valve 14 assembly and the second crushable chemical insert 28 to prevent any of the first substance 26a, or the second substance 28a, or the by-products of the chemical reaction from contaminating the valve 14 assembly.

Referring now primarily to FIG. 3, is shown an alternative embodiment consisting of a larger outer deformable capsule 38 containing a smaller inner crushable capsule 40 therein. A third substance 38a is dispersed within the outer capsule 38 and a fourth substance 40a is dispersed within the inner capsule 40 such that when the third substance 38a and the fourth substance 40a are combined, an exothermic chemical reaction occurs.

The outer capsule 38 is suspended within the cylinder 12 by a pair of retaining rings 42a, 42b, each of which are disposed at opposite ends of the outer capsule 38. Although it is not visible in the FIG. 3 drawing, both of the pair of retaining rings 42a, 42b must each contain air passage holes (not shown), that allow for the passage of ambient air (vapor) through the pair of retaining rings 42a, 42b, similar to the holes 18 in the disk 16. Vapor must also be allowed to pass around the outer capsule 38 and therefore the outside diameter of the outer capsule 38 must be less than inside diameter of the cylinder 12.

This particular configuration is utilized when either the third substance 38a or the fourth substance 40a or the resultant by-products of the exothermic chemical reaction are regarded as being either noxious, toxic, offensive, or under suspicion of being such. The advantage of this embodiment is that the outer capsule 38, being deformable and yet highly resistant to rupturing, provides a means of containment for either the third substance 38a, the fourth substance 40a, the by-products of the exothermic reaction, or for any combination of the above.

When the simulated heated cigarette 10 is squeezed near the middle of the cylinder 12, the cylinder 12 and the outer capsule 38 deform until the inner crushable capsule 40 has been ruptured. When the inner crushable capsule 40 has been ruptured the fourth substance 40a contained therein is released into the outer capsule 38 where it can combine and chemically react with the third substance 38a. Both the third substance 38a, the fourth substance 40a, and all chemical by-products of the exothermic reaction are contained within the outer capsule 38.

A second inner capsule 42 that can be ruptured containing a fifth substance 42a therein is included to illustrate that tertiary exothermic chemical reactions are anticipated as well as the more common binary reactions. A tertiary exothermic chemical reaction involves the admixture of three separate substances, which when combined, chemically react to produce heat, whereas a binary exothermic reaction involves the admixture of two separate substances.

A tertiary reaction may be preferred if the substances thus utilized are especially harmless when separated, or if other advantages, such as lower cost, greater shelf-life (storage time), or a greater or a prolonged generation of heat are achieved.

Similarly if more than three substances are preferred to remain segregated until use (mixing), the incorporation of any number of additional capsules (not shown) is anticipated. Similarly if three or more capsules are used, they do not have to be contained within the larger deformable outer capsule 38, but may instead be placed adjacent to each other in a manner consistent with the teachings of FIG. 1.

The spring 24, useful to better hold the rubber disk 22 adjacent to the disk 16, is shown in the FIG. 3 drawing as being in contact at one end thereof with one end of the outer capsule 38 and being in contact at the remaining end thereof with the rubber disk 22, thus securing it in a position of cooperation with the rubber disk 22.

As neither the third substance 38a, the fourth substance 40a, nor the by-products of the exothermic reaction are able to mix with the vapor, there is no need for an inlet screen 37, and accordingly it is absent from the FIG. 3 drawing.

A thermometer 44 is useful to indicate proper operation of the simulated heated cigarette 10 and may be incorporated into either embodiment as disclosed. The thermometer may reflect the surface temperature of the cylinder 12 or it may include a thermocouple 46 as the means to sense the temperature within the cylinder 12. The thermometer 44, as shown, may reflect a range of temperatures or it may simply indicate that a temperature above or below a particular point, for example 85 degrees Fahrenheit, has been attained. A temperature below this point would indicate either that the simulated heated cigarette 10 has not yet been properly started or that the chemicals therein are consumed, and hence the use of the simulated heated cigarette 10 is finished. Any particular temperature, either higher or lower than used in the above example, may of course be used to indicate proper operation by the thermometer 44.

A modified filter 48 is shown. The modified filter 48 has itself been treated so as to contain a flavoring 50 therein. The flavoring 50 is represented in the FIG. 3 drawing as a series of dots disposed within the modified filter 48. An example for the flavoring 50 is a retail product known as "LIQUID SMOKE" which would add a smoky flavor to the modified filter 48 if the modified filter were saturated with this product.

Of course, the first screen 30 and the second screen 32 along with the desired substance 34 of FIG. 1 may be used in this embodiment instead of the modified filter 48.

Operation:

In use the simulated heated cigarette 10 is grasped near to its center by a user who repeatedly squeezes it until he is certain he has ruptured any and all interior capsules (which include the first crushable chemical insert 26 and the second crushable chemical insert 28, or the inner crushable capsule 40, and possibly the second inner capsule 42. If the thermometer 44 is present, he may wish to consult it to verify that a proper operating temperature has been reached after which time he may begin to inhale from the outlet end 12b in a manner similar to that of smoking the conventional type of a cigarette. When he has either satisfied himself or the temperature has fallen (indicating that the simulated heated cigarette 10 is effectively consumed) it is then discarded. Even if the simulated heated cigarette 10 has not completed its chemical reaction, it may still be safely discarded as the temperatures involved do not pose a combustion hazard.

If the user is utilizing the simulated heated cigarette 10 to consume a prescribed medication, he would of course follow the prescription dictates as to frequency of use and quantity of simulated heated cigarettes 10 consumed.

If the user is utilizing the simulated heated cigarette 10 to taper off from smoking he would progressively, over time, switch to ever decreasing nicotine levels in the simulated heated cigarette 10 until he has either lost entirely the craving for nicotine or until he is presently satisfied with his level of consumption. Accordingly, the simulated heated cigarette 10 would be packaged in decreasing nicotine concentrations as desired.

The invention has been shown, described and illustrated in substantial detail with reference to the presently preferred embodiment. It will be understood by those skilled in this art that other and further changes and modifications may be made without departing from the spirit and scope of the invention which is defined by the claims appended hereto.

What is claimed is:

1. A simulated cigarette, comprising:
   (a) a cylinder having a first end and a second end, at least a portion of said cylinder being deformable, said portion being disposed intermediate said first end and said second end;
   (b) valve means disposed in said cylinder near to said first end;
   (c) at least a pair of capsules in said cylinder, at least one of said pair of capsules being rupturable upon a compressive force being applied thereto by applying a compressive force to the outside of said cylinder sufficient to deform said portion of said cylinder, each of said at least a pair of capsules containing a substance therein that, when combined together, react chemically in such a manner as to produce heat; and
   (d) means to provide a filter disposed in said cylinder near to said second end.

2. The simulated cigarette of claim 1 including a desired substance, said desired substance disposed in said cylinder intermediate said means to provide a filter and said at least a pair of capsules.

3. The simulated cigarette of claim 2 wherein said desired substance includes a flavor enhancing material.

4. The simulated cigarette of claim 2 wherein said desired substance includes a therapeutic substance.

5. The simulated cigarette of claim 2 wherein said desired substance includes tobacco.

6. The simulated cigarette of claim 2 wherein said desired substance includes an insert containing nicotine.

7. The simulated cigarette of claim 1 wherein said at least a pair of capsules includes a larger outer capsule and at least one inner capsule, said at least one inner capsule disposed within said outer capsule, said outer capsule being deformable but resistant to rupturing, and said at least one inner capsule having a tendency to rupture upon a compressive force being applied thereto.

8. The simulated cigarette of claim 1 wherein said means to provide a filter includes a first screen.

9. The simulated cigarette of claim 8 including a second screen, said second screen disposed a predetermined distance from said first screen so as to define a space between said first screen and said second screen.

10. The simulated cigarette of claim 9 wherein a desired substance is included in said space.

11. The simulated cigarette of claim 10 wherein said desired substance includes a flavor enhancing material.

12. The simulated cigarette of claim 10 wherein said desired substance includes a therapeutic substance.

13. The simulated cigarette of claim 10 wherein said desired substance includes tobacco.

14. The simulated cigarette of claim 10 wherein said desired substance includes an insert containing nicotine.

15. The simulated cigarette of claim 1 wherein said valve means is a check valve that permits the flow of a vapor in a direction from said first end to said second end of said cylinder and prevents the flow of said vapor in a direction from said second end to said first end of said cylinder.

16. The simulated cigarette of claim 15 wherein said valve means includes a disk having at least one hole therein and a flexible disk attached to said disk, said flexible disk permitting the flow of a vapor to occur through said disk in a direction from said first end to said second end of said cylinder and preventing the flow of said vapor through said disk in a direction from said second end to said first end of said cylinder.

17. The simulated cigarette of claim 15 wherein said valve means includes a spring.

18. The simulated cigarette of claim 1 including an inlet screen, said inlet screen disposed intermediate to said valve means and said at least a pair of capsules.

19. The simulated cigarette of claim 1 wherein said means to provide a filter includes a modified filter that contains a flavoring.

20. The simulated cigarette of claim 1 including a thermometer.

* * * * *